US00PP27811P3

(12) United States Plant Patent
Schuster

(10) Patent No.: US PP27,811 P3
(45) Date of Patent: Mar. 28, 2017

(54) VARIETY OF CHERRY TREE NAMED 'AREKO'

(50) Latin Name: *Prunus avium*
Varietal Denomination: Areko

(71) Applicant: Julius Kühn-Institut (JKI), Federal Research Centre for Cultivated Plants, Quedlinburg (DE)

(72) Inventor: Mirko Schuster, Dresden (DE)

(73) Assignee: Julius Kühn-Institut (JKI), Federal Research Centre for Cultivated Plants, Quedlinburg (DE)

( * ) Notice: Subject to any disclaimer, the term of this patent is extended or adjusted under 35 U.S.C. 154(b) by 145 days.

(21) Appl. No.: 14/121,482

(22) Filed: Sep. 10, 2014

(65) Prior Publication Data

US 2016/0073562 P1 Mar. 10, 2016

(51) Int. Cl.
*A01H 5/08* (2006.01)

(52) U.S. Cl.
USPC ..... Plt./181

(58) Field of Classification Search
USPC ..... Plt./181
See application file for complete search history.

*Primary Examiner* — Keith Robinson
(74) *Attorney, Agent, or Firm* — The Webb Law Firm

(57) ABSTRACT

A new and distinct cherry tree that produces sweet cherry fruits with very good eating qualities.

6 Drawing Sheets

Botanical classification: *Prunus avium.*
Varietal denomination: 'Areko'.

BACKGROUND OF THE INVENTION

The present invention comprises a new and distinct cultivar of *Prunus avium* known by the varietal name 'Areko' (also internally referred to as "Hamid"). The new variety was discovered in Dresden, Germany after many years of controlled breeding. The new variety is the result of a planned breeding program between cherry trees named 'Kordia' (female parent, unpatented) and 'Regina' (male parent, unpatented). The new variety is similar to 'Kordia' in ripening time and 'Regina' in fruit size. The new variety differs from its parental varieties in having a pointed fruit pistil end and an overall cordate fruit shape. When further compared to 'Kordia', the new variety is similar in fruit color, but has a heavier fruit weight and lighter red color of its fruit flesh than 'Kordia'. The purpose of breeding the new variety was to provide cherries with improved fruit quality. The new variety was first asexually reproduced via grafting in Ahrensburg, Germany. The new variety has been trial and field tested and has been found to retain its distinctive characteristics and remain true to type through successive propagations. The following characteristics distinguish the new variety from other unpatented cherry tree varieties known to the breeder:

1. 'Lapin'—Blooming time (early);
2. 'Krupnoplodnaja'—Fruit shape (reniform);
3. 'Burlat'—Ripening time (early);
4. 'Staccato'—Ripening time (very late);
5. 'Büttners Rote Knorpelkirsche'—Fruit color; and
6. 'Vanda'—Fruit shape (reniform).

DESCRIPTION OF THE DRAWINGS

The accompanying photographic drawings illustrate the new variety taken at its fifth leafing, with the color being as nearly true as is possible with color illustrations of this type.

DETAILED BOTANICAL DESCRIPTION

Figure 1:
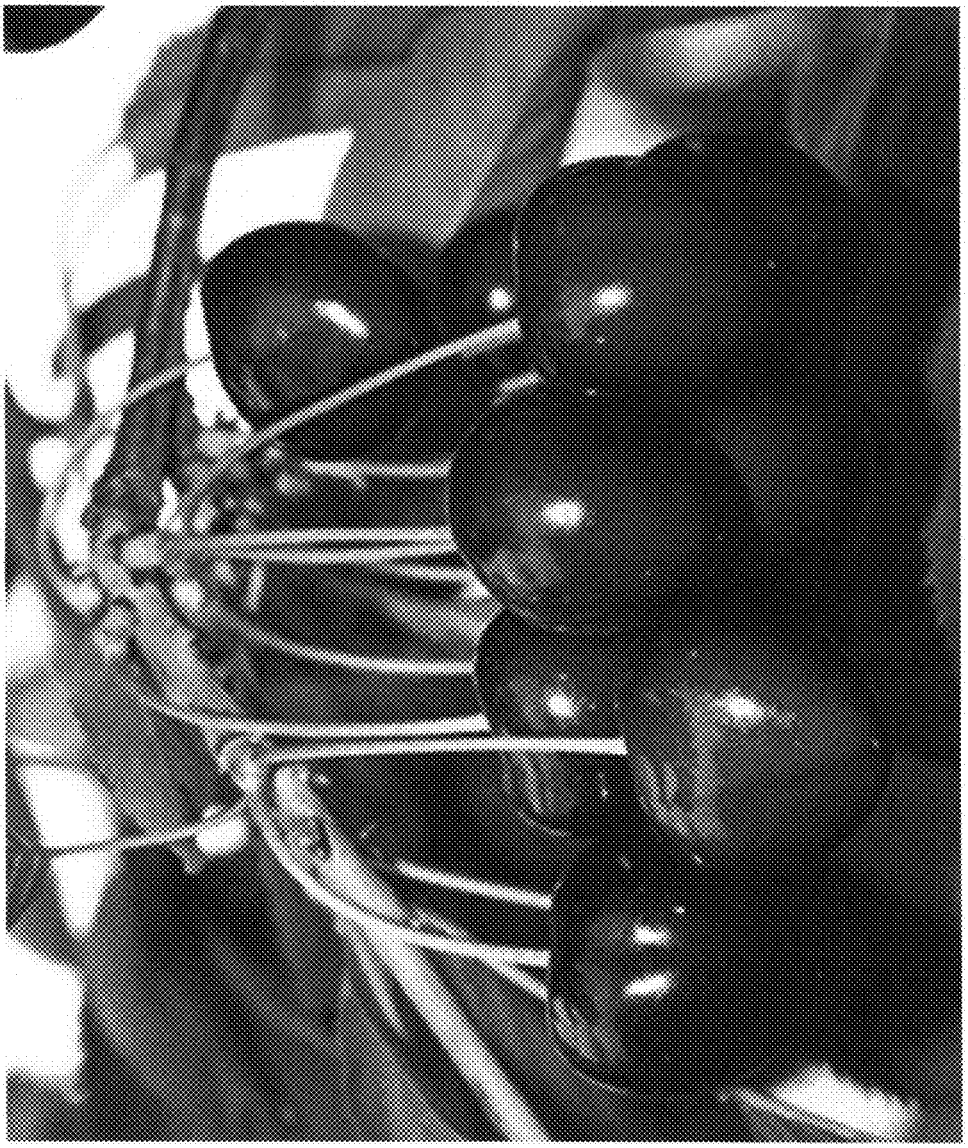
FIG. 1 is a close-up photograph of the fruit of 'Areko'.
Figure 2:
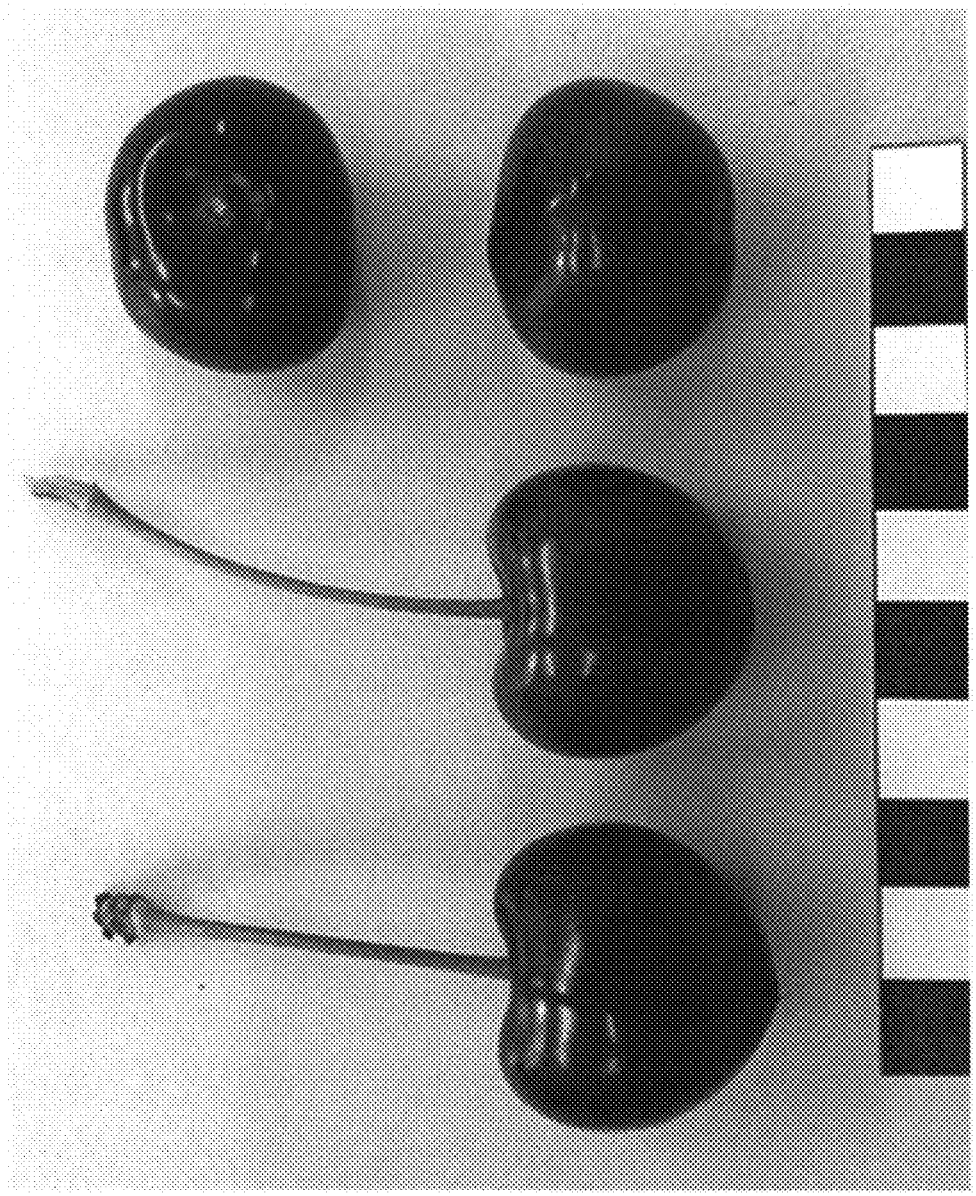
FIG. 2 is a further close-up photograph of the fruit of 'Areko'.
Figure 3:
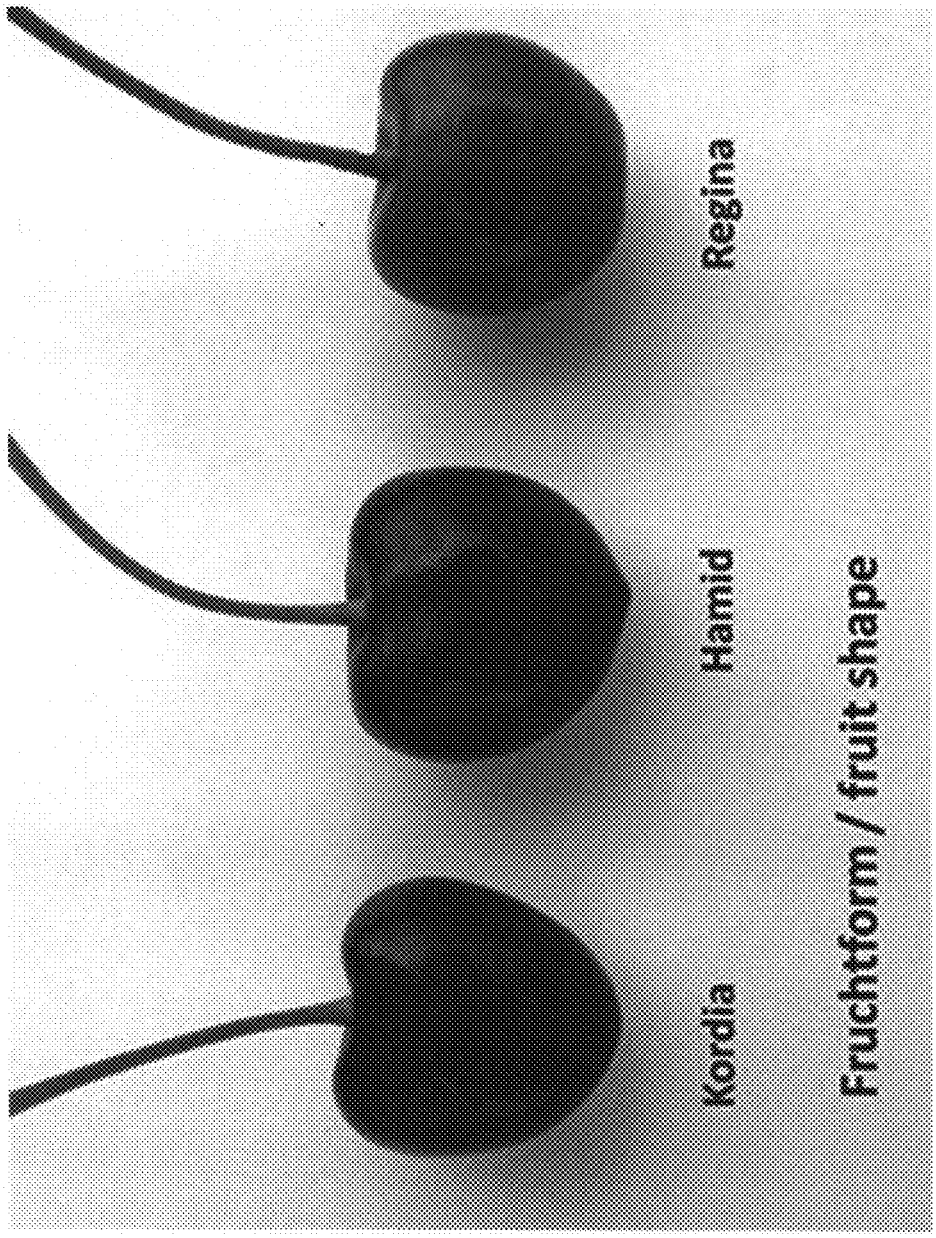
FIG. 3 is a comparative photograph of the fruit of 'Areko' ("Hamid")
Figure 4:
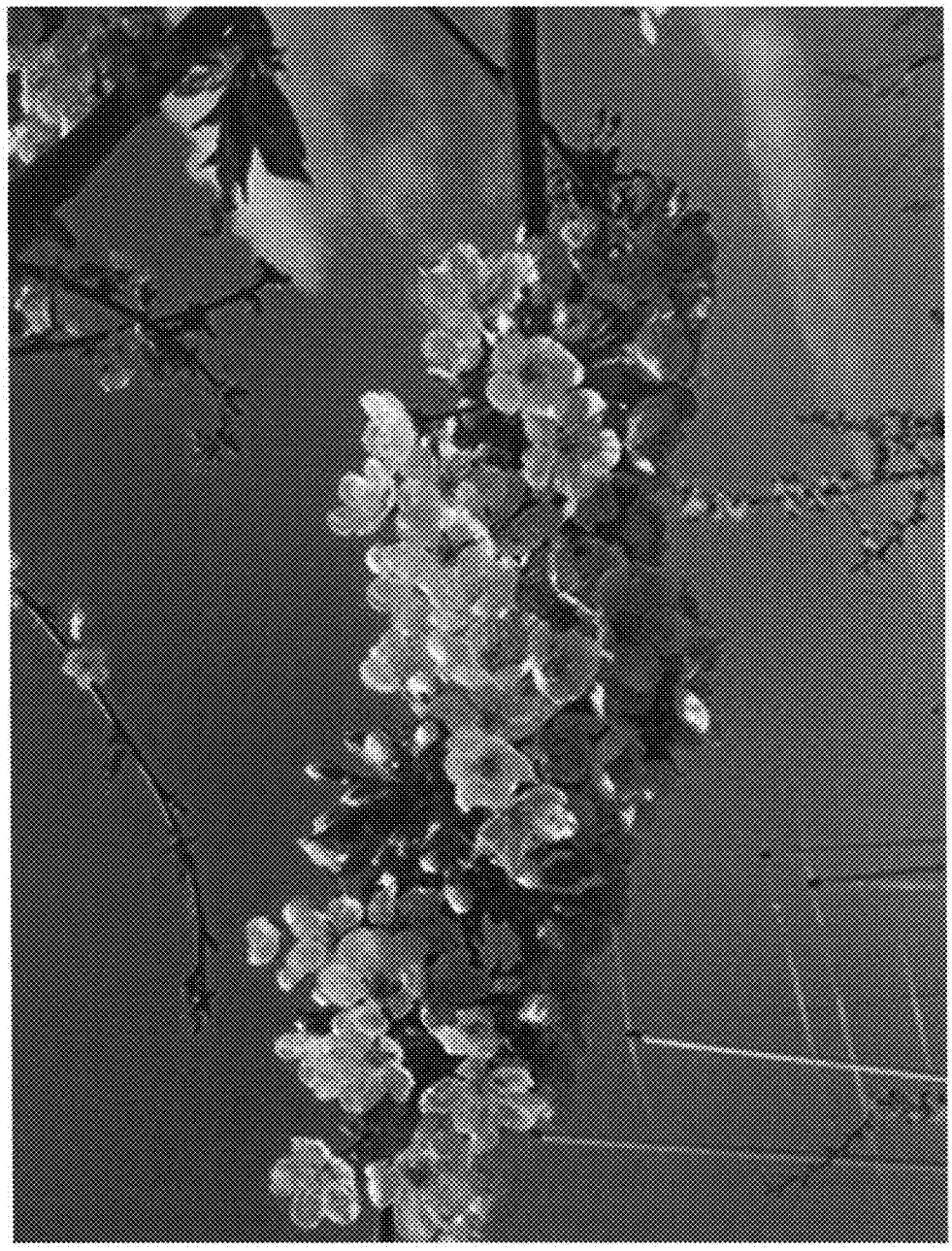
FIG. 4 is a photograph of the flowers of 'Areko'.
Figure 5:
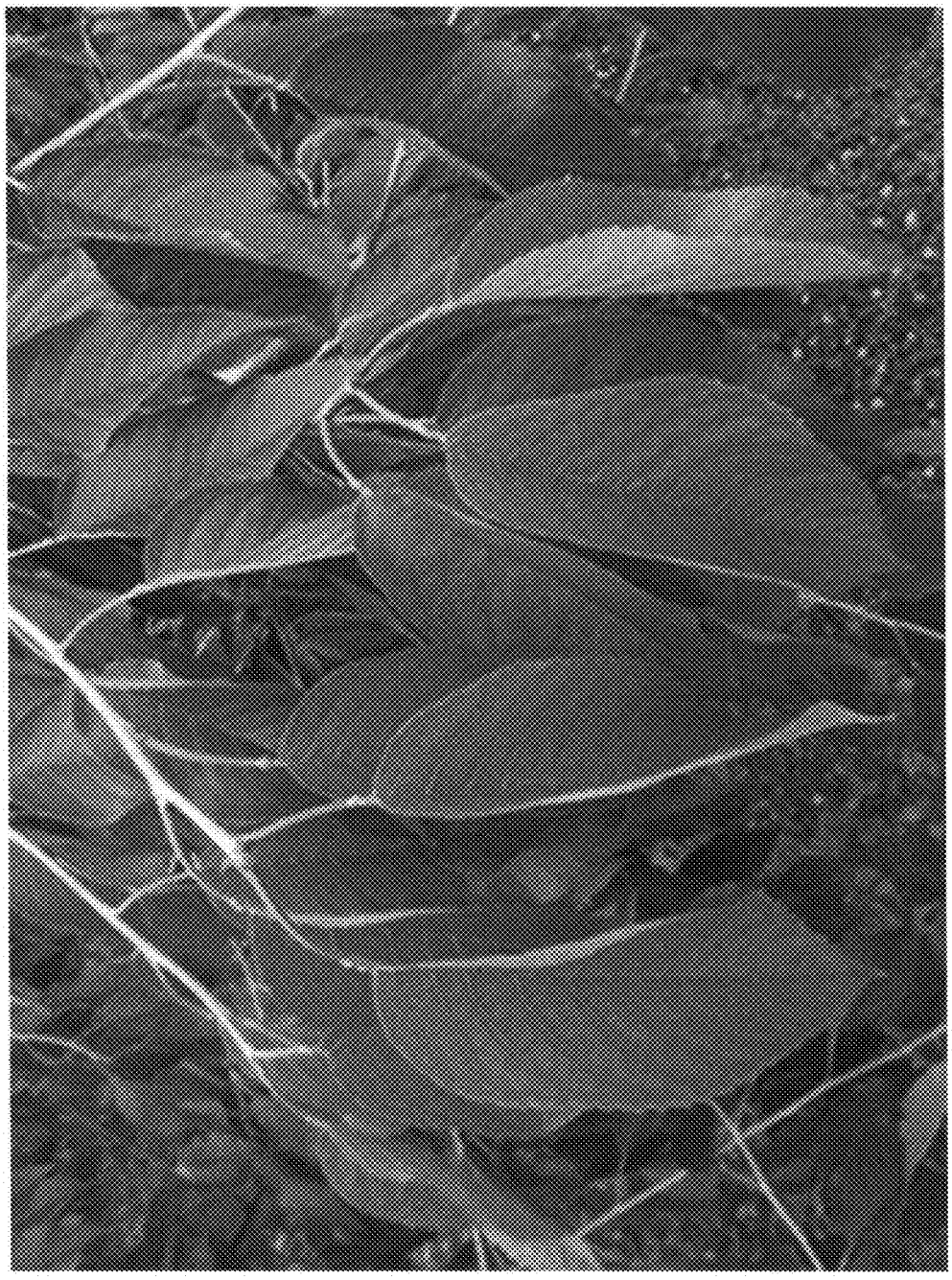
FIG. 5 is a close-up photograph of the leaves of 'Areko'.
Figure 6:
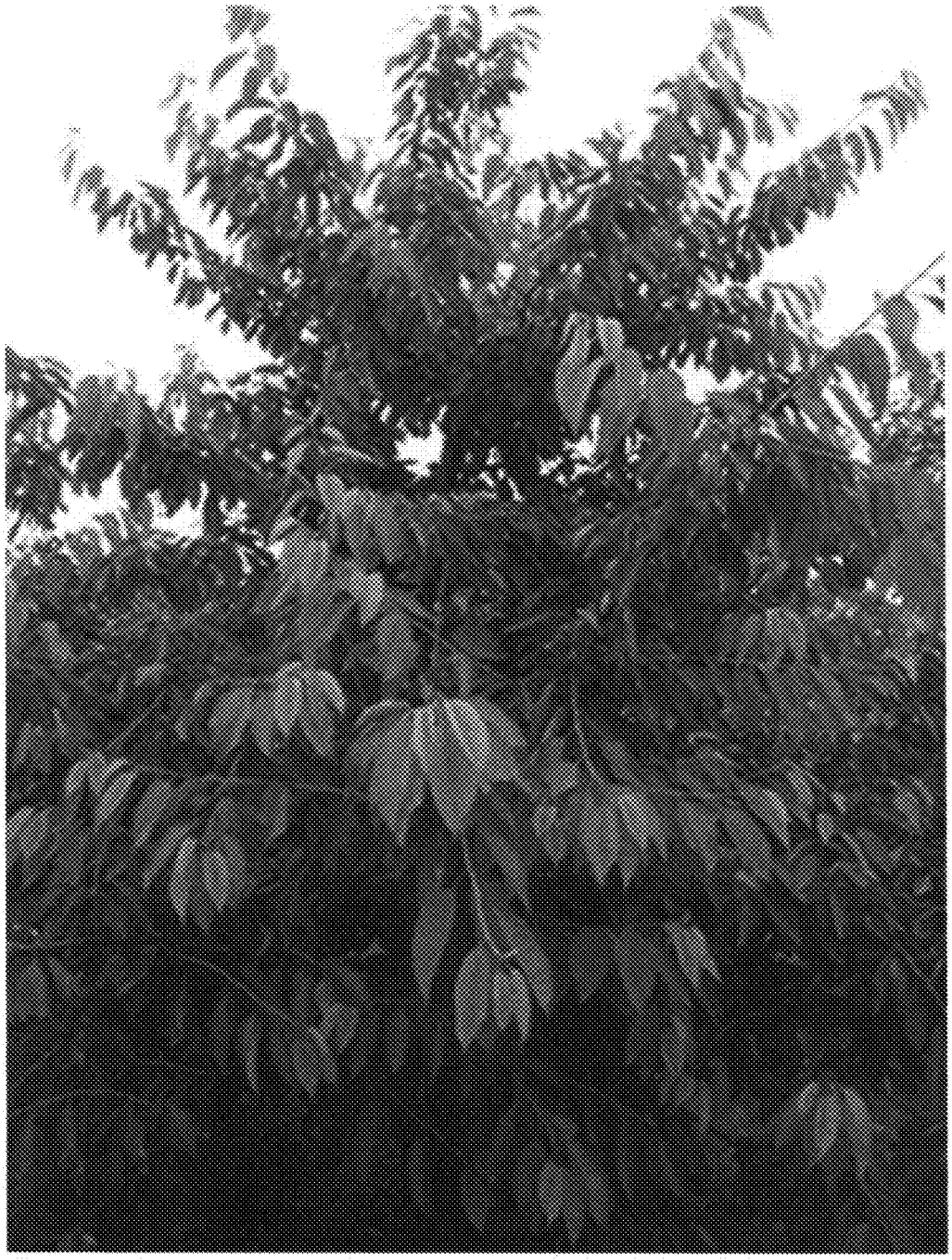
FIG. 6 is a photograph of an entire tree of 'Areko'.

The following detailed description sets forth the characteristics of the new cultivar. The new variety was grown under standard cherry tree growing conditions using a central leader (spindle) training system in Dresden, Germany. Fungicide and insecticide treatments were provided according to general recommendations. The color readings were taken in natural daylight, and the plant was 7 years old when described. Except where indicated elsewhere, the color standards are the $6^{th}$ edition (2015) of The Royal Horticultural Society (R.H.S.) of London Colour Chart, as well as the #6 color chip of the Centre Technique Interprofessionnel des Fruits (CTIFL) color chart.

Tree:

*Height.*—2.5-3.0 m.
*Spread.*—2.5-4.5 m.
*Vigor.*—Medium.
*Habit.*—Spreading.
*Growth type.*—Central leader, spindle.
*Branching.*—Medium.
*Petiole.*—Length: 2.6-5.5 cm (average of 4.3 cm). Diameter: 1.5-2 mm. Texture: Bumpy. Color: N34A along the majority of the length, ending in 144B at the leaf base.

Color of nectaries: N34A.

Leaves:

*Length.*—17.2 cm.

*Width.*—8.5 cm.
*Form.*—Broad and obovate.
*Base.*—Acute.
*Apex.*—Apiculate (acute).
*Margin.*—Dentate with symmetrical teeth.
*Pubescence.*—Upper surface: None. Lower surface: Present on veins.
*Color.*—Young leaves: Upper surface: 144A. Lower surface: 144D. Mature leaves: Upper surface: 137A. Lower surface: 138B.
*Venation.*—Type: Dichotomous. Color: Upper surface: 145B. Lower surface: 145C.

Flowers:
*Blooming timing.*—Late.
*Pollination requirements.*—Necessary, Incompatibility Group II.
*Diameter.*—4.5 cm.
*Petals.*—Number: 5. Shape: Circular. Length: Approximately 1.8 cm. Width: Approximately 1.7 cm. Arrangement: Overlapping. Margin: Entire. Texture: Unruffled. Color (when opening and fully opened): Upper surface: White; approximately NN155D from the 5$^{th}$ edition (2007) of The R.H.S. Colour Chart. Lower surface: White; approximately NN155D from the 5$^{th}$ edition (2007) of The R.H.S. Colour Chart.
*Reproductive organs.*—Stamens: Average of 30-32 per flower. Anthers: 11A in color. Pollen: 12B in color and high in amount. Stigma: 144D in color:

Fruit:
*Time of beginning of fruit ripening.*—16 days later than cherry tree variety 'Burlat' (unpatented), which has an early ripening time.
*Shape.*—Cordate and pointed at the pistil end.
*Size.*—Diameter: 29.4 mm.
*Skin.*—Tendency to crack: Intermediate. Color: Dark red (6CTIFL). Ground color: 44B with medium-sized lenticels present.
*Flesh.*—Aroma: Present. Color: Dark red (6CTIFL) to black red (7CTIFL). Texture: Firm. Eating quality: Very good.
*Seeds.*—Number per fruit: 1. Length: Average of 13.4 mm. Width: Average of 9.9 mm. Diameter: Average of 8.0 mm. Form: Circular. Color: 159C.
*Stalk.*—Length: Average of 55 mm.Thickness: Medium. Color: 140B.

Tree winter hardiness: Good.
Bud winter hardiness: Good.
Drought tolerance: Unknown.
Disease/pest resistance or susceptibility: Unknown.

I claim:
1. A new and distinct variety of cherry tree, as is herein illustrated and described.

* * * * *